United States Patent [19]
Hatton et al.

[11] Patent Number: 5,483,171
[45] Date of Patent: Jan. 9, 1996

[54] DETERMINATION OF WATER CUT AND GAS-FRACTION IN OIL/WATER/GAS STREAMS

[75] Inventors: Gregory J. Hatton, Kingwood; David A. Helms; John D. Marrelli, both of Houston, all of Tex.

[73] Assignee: Texaco Inc., White Plains, N.Y.

[21] Appl. No.: 301,942

[22] Filed: Sep. 7, 1994

[51] Int. Cl.[6] .................................................. G01N 22/04
[52] U.S. Cl. ........................ 324/640; 73/61.44; 324/698
[58] Field of Search ................................. 324/640, 698, 324/639, 637; 73/61.41, 61.44

[56] References Cited

U.S. PATENT DOCUMENTS

| | | | |
|---|---|---|---|
| 4,137,495 | 1/1979 | Brown | 324/698 |
| 4,203,817 | 5/1980 | Schutt | 73/61.41 |
| 4,644,263 | 2/1987 | Johnson | 324/698 |
| 5,001,434 | 3/1991 | Marrelli et al. | 324/640 |
| 5,157,339 | 10/1992 | Scott et al. | 324/639 |
| 5,286,375 | 2/1994 | Marrelli | 324/640 |
| 5,363,696 | 11/1994 | Cardinelli | 73/61.44 |
| 5,369,368 | 11/1994 | Kassen et al. | 324/640 |
| 5,408,868 | 4/1995 | Ortega et al. | 73/61.41 |

FOREIGN PATENT DOCUMENTS 3542238  4/1987  Germany ................................ 324/698

*Primary Examiner*—Maura K. Regan
*Attorney, Agent, or Firm*—James L. Bailey; Kenneth R. Priem; William J. Beard

[57] ABSTRACT

A great many small volume samples are taken, at a high rate of frequency, from a multi-phase fluid stream to determine the respective oil, water and gas fractions. Rapid fluctuations from an all liquid curve will indicate the presence of gas in the fluid.

3 Claims, 1 Drawing Sheet

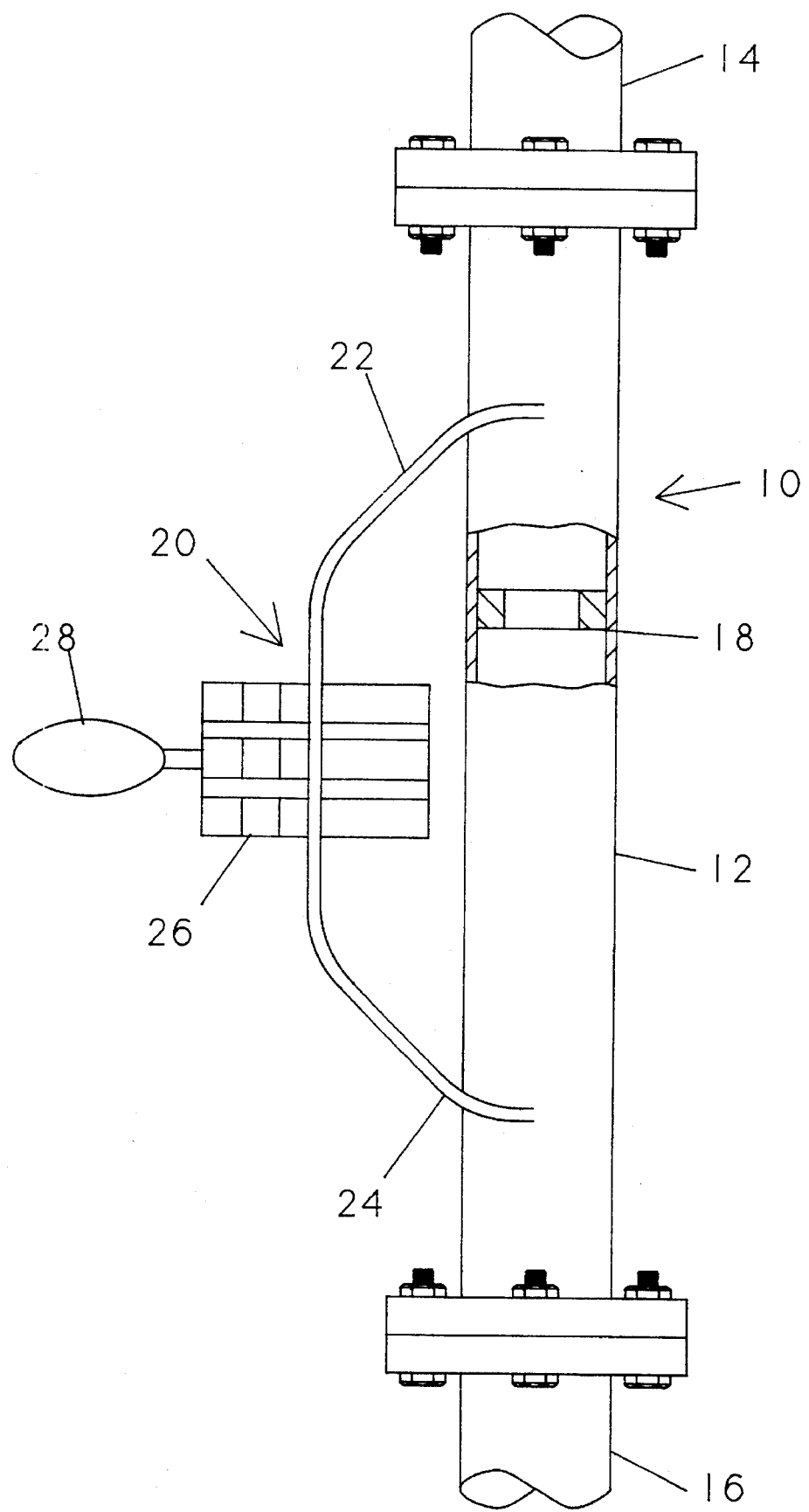

5,483,171

DETERMINATION OF WATER CUT AND GAS-FRACTION IN OIL/WATER/GAS STREAMS

BACKGROUND OF THE INVENTION

1. The Field of the Invention

The present invention pertains to a method and apparatus to rapidly measure the changing properties of flowing water, oil, and gas mixtures, and in particular to a system which takes very rapid, small volume measurements.

2. The Prior Art

There has been a great deal of effort put into the development and improvement of techniques for determining water cut and gas-fraction in oil/water/gas streams using dielectric probes in pipes of 2-inch diameter, or larger, containing a well mixed fluid In this content, "well mixed" means that the fluid is homogeneous with respect to the two inch pipe volume and that the time scale is less than one second. While it is possible to determine gas-fraction and water cut with a dielectric measure of a homogeneous mixture of the oil/water/gas stream, this homogeneous mixture measurement is often augmented by another measurement, such as a density measurement, to determine water cut and gas-fraction. Examples of this can be found in U.S. Pat. No. 5,101,164, the disclosure of which is incorporated herein by reference.

The present inventors have discovered that despite large scale homogeneity, there also is small scale heterogeneity which can be exploited to great advantage by making a large number of rapid small scale measurements.

SUMMARY OF THE INVENTION

The present invention is a method for determining the water cut and gas fraction of oil/water/gas streams by taking many rapid small volume measurements from a flowing multi-phase fluid stream and determining nonhomogeneous regions in the supposedly homogeneous stream, these regions being then used to determine oil, water, and gas fractions.

BRIEF DESCRIPTION OF THE DRAWINGS

The present invention will now be described, by way of example, with reference to the accompany drawings wherein the single FIGURE is a schematic representation of a side stream sampling device of a type suitable to practice the present invention.

DETAILED DESCRIPTION OF THE PREFERRED EMBODIMENT

A known side stream sampling device 10 is shown in FIG. 1 and is along the lines of the water cut monitor described in U.S. Pat. No. 5,001,434, the disclosure of which is incorporated herein by reference. The device includes a pipe segment 12 mounted between pipes 14, 16 of a fluid distribution system (not shown). A known flow restriction means 18, such as the illustrated orifice plate, is fixed within pipe segment 12 to cause pressure build up so that at least part of the multi-phase fluid flow will pass through the sampling means 20. First and second sampling tubes 22, 24 each have one end opening into pipe segment 12 on opposite sides of the flow restriction means 18, and their opposite ends opening into a test cell 26. Either or both sampling tubes can be provided with valve means (not shown) if it is desired to isolate the test cell 26. The test cell 26 can be of known type, such as that described in U.S. Pat. No. 4,947,127, the disclosure of which is also incorporated herein by reference. The test cell 26 preferably provides for sample and reference microwaves and includes a temperature transducer 28. It is to be understood that this drawing is extremely simplified and that many conventional things, such as the above mentioned valves, have not been illustrated but would be understood by those skilled in the art.

The device extracts a small stream of fluid from the main line on one side of the flow restriction means 18, passes it through the test cell 26 and then returns the sample to the main line on the opposite side of the flow restriction means 18. The velocity of the flow in the test cell 26 is governed by the flow restriction means 18 in the main line 12 and the diameter of the test cell pipes 22, 24. Normal fluid flow in such devices is approximately 8 feet per second, and the measurements are preferably taken at a rate of 200 per second. The volume of the measurement is preferably less than a cubic inch, usually ¼"×¼"×½". The goal is to very rapidly measure a great number of volumes the fluid of sufficiently small size that individual bubbles within the fluid flow will be measured.

The present invention utilizes a sampling apparatus, such as the above described one, to make very rapid and small volume measurements in a flowing multi-phase fluid mixture stream. This takes advantage of the small scale heterogeneity present in the stream and obtains a range of sample measurements from substantially total liquid (when no bubbles are present in the sample) to substantially total gas (when only a bubble is present). The oil, gas, pure water, and pure oil dielectric properties can then each be determined with dielectric measurement of these very small volumes. These very rapid measurements, preferably taken at rates of faster than once per second, can even be taken at rates as high as 500 times per second. The small volume of the sample is preferably taken from a sample pipe of less than 2" in diameter and preferably a pipe of approximately ¼" in diameter. This rapid and small scale approach allows for real time characterization of the constantly changing fundamental properties of oil field fluids, such as the dielectric contents of the currently flowing water, oil, and gas fluid mixtures.

This is accomplished in the following manner. The oil/water/gas stream dielectric properties are measures quickly enough and on a sample small enough to measure the individual gas bubbles. This can be arranged using a slip or sample stream from a larger or main stream. When measured in this manner, a large set of measured values for the dielectric is obtained. This corresponds to the set of different oil/water/gas samples measured; some of which have no gas, some of which have little gas, and some of which have more gas. As long as the stream remains liquid continuous, large and larger gas fractions result in dielectric measurements which are further and further from the gas-free dielectric measurement. This allows the gas-free dielectric values which form a curve mapping different water cuts of the particular water and oil dielectrics being measured. The oil/water/gas dielectric values all lie to one side of the gas-free curve. It should be here noted that there are really two gas free curves; an oil-continuous curve and water-continuous curve. This is only a minor inconvenience which is overcome by having two sets of curves; one for an oil continuous condition and one for a water continuous condition.

The present invention may be subject to many modifications and changes without departing from the spirit or essential characteristics thereof. The present embodiment should therefor be considered in all respects as being illustrative and not restrictive as to the scope of the present invention.

We claim:

1. A method for determining the water cut and gas fraction of grossly homogeneous oil/water/gas streams, comprising the steps of:

repetitively, at a rate of several times per second taking a large number of discrete small volume samples from said stream; and measuring the microwave frequency dielectric properties of each sample whereby fluctuations in these measurements indicate the presence of relatively small volume nonhomogeneous regions in grossly homogeneous streams to thereby obtain accurate oil, water and gas fractions.

2. The method according to claim 1 wherein fluctuations in the measurements indicate the presence of at least one gas bubble in the grossly homogeneous fluid.

3. An apparatus for determining the water cut and gas fraction of a grossly homogeneous oil/water/gas stream comprising:

means for repetitively taking small samples of a grossly homogeneous multi-phase fluid at a rate of several samples per second; and means for measuring microwave frequency dielectric properties of each said sample whereby fluctuations of the measurements indicate the presence of gas bubbles in the grossly homogeneous multi-phase fluid.

* * * * *